US007342495B2

(12) United States Patent
Sayegh

(10) Patent No.: US 7,342,495 B2
(45) Date of Patent: Mar. 11, 2008

(54) INTEGRATED THEFT DETERRENT DEVICE

(76) Inventor: Adel O. Sayegh, 5143 Paddock Pl., Rancho Cucamonga, CA (US) 97137

( * ) Notice: Subject to any disclaimer, the term of this patent is extended or adjusted under 35 U.S.C. 154(b) by 0 days.

(21) Appl. No.: 10/860,346

(22) Filed: Jun. 2, 2004

(65) Prior Publication Data

US 2005/0270155 A1 Dec. 8, 2005

(51) Int. Cl.
*G08B 13/14* (2006.01)
*E05B 47/00* (2006.01)
*G16B 21/00* (2006.01)

(52) U.S. Cl. ................................ 340/572.1; 340/568.1; 340/568.2; 340/572.8; 340/572.9; 70/276; 70/282; 24/704.1; 24/704.2

(58) Field of Classification Search ............ 340/568.1, 340/568.2, 572.1, 572.8, 572.9; 70/282, 70/276; 24/704.1, 704.2, 706.2
See application file for complete search history.

(56) References Cited

U.S. PATENT DOCUMENTS

| | | | | |
|---|---|---|---|---|
| 3,858,280 A | | 1/1975 | Martens | |
| 3,911,534 A | | 10/1975 | Martens et al. | |
| 3,932,918 A | | 1/1976 | Paskert | |
| 3,942,829 A | | 3/1976 | Humble et al. | |
| 3,974,581 A | | 8/1976 | Martens et al. | |
| 4,221,025 A | | 9/1980 | Martens et al. | |
| 4,588,218 A | * | 5/1986 | Guiler et al. | 292/307 R |
| 5,610,587 A | * | 3/1997 | Fujiuchi et al. | 340/568.2 |
| 6,535,130 B2 | | 3/2003 | Nguyen et al. | |

* cited by examiner

*Primary Examiner*—Julie Lieu
(74) *Attorney, Agent, or Firm*—Milord A. Keshishian

(57) ABSTRACT

An integrated theft deterrent tag 20 having a lanyard 38 emanating therefrom. The lanyard 38 having a pin 48 permanently attached thereto and the pin 48 being received within a locking mechanism 32 and enclosing an article to be protected.

18 Claims, 5 Drawing Sheets

FIG 7
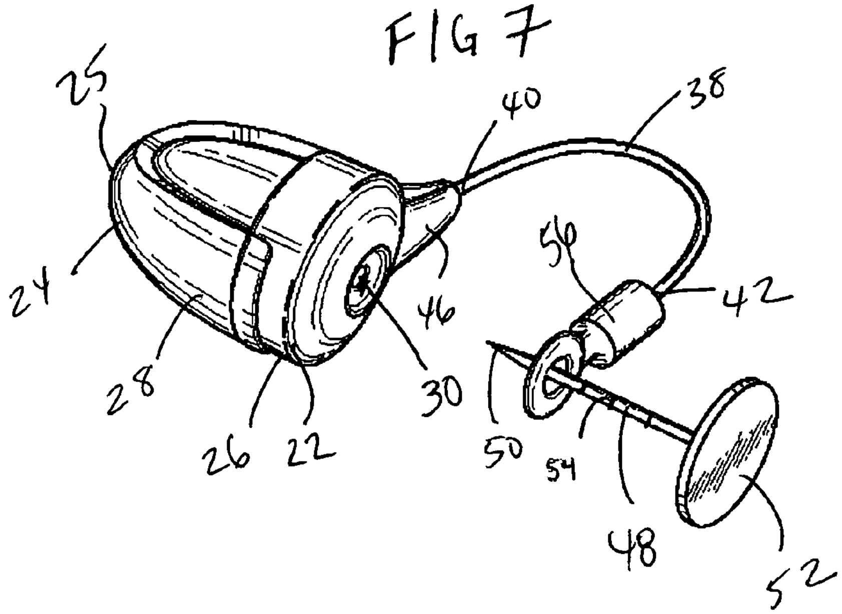
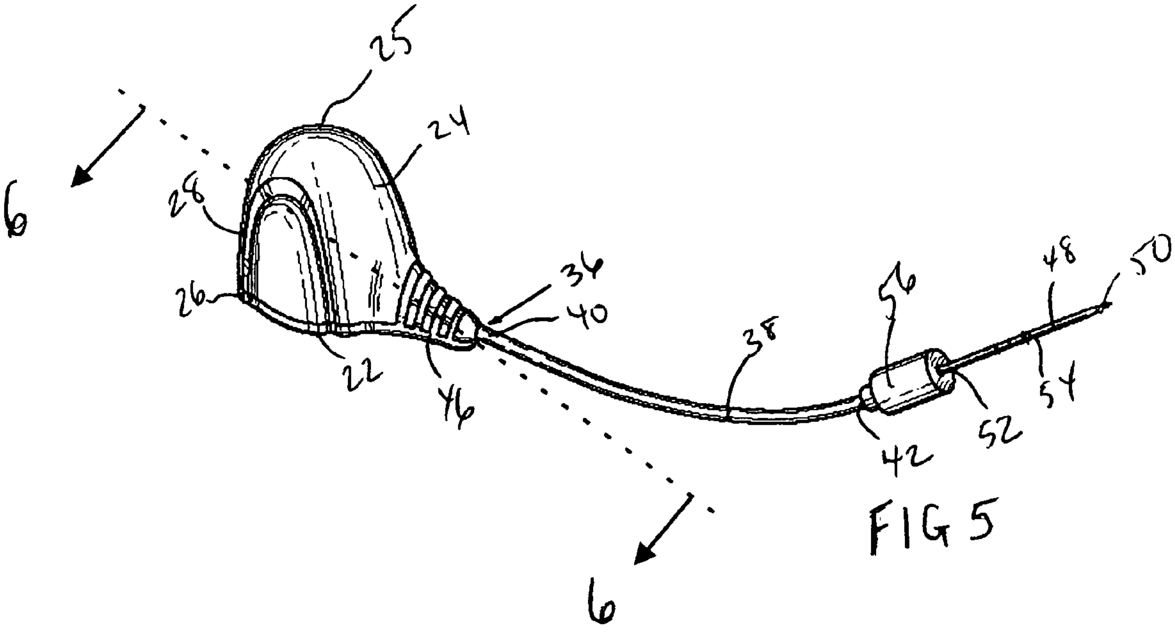
FIG 5

INTEGRATED THEFT DETERRENT DEVICE

CROSS-REFERENCE TO RELATED APPLICATIONS

The contents of this application are related to U.S. design patent applications having Ser. Nos. 29/182,901, 29/182,878, and 29/182,914, filed on Jun. 2, 2003, the contents of which are incorporated herein by reference.

FIELD OF THE INVENTION

The invention relates to theft deterrent security tags in general, and in particular to an integrated security tag containing an attaching pin that emanates from the tag body for use in electronic article surveillance (EAS) tags for theft deterrence.

BACKGROUND OF THE INVENTION

Various types of electronic article surveillance (EAS) systems are known having the common feature of employing a marker or tag which is affixed to an article to be protected against theft from a controlled area, such as merchandise in a store. When a legitimate purchase of the article is made, the marker can either be removed from the article, or converted from an activated state to a deactivated state. Such systems employ a detection arrangement, commonly placed at all exits of a store, and if an activated marker passes through the detection system, it is detected by the detection system and an alarm is triggered.

Such electronic detection arrangements, as used in the present invention, are well known in the art and are more clearly discussed in my co-pending U.S. patent application Ser. No. 10/410,486, titled "Article Surveillance Tag Having a Metal Clip," filed on Apr. 8, 2003, which is incorporated herein by reference. In addition, the locking mechanism and removal tool, as used in the instant invention, are also well known in the art and are disclosed in U.S. Pat. No. 3,588,280 to Martin A. J. Marens and U.S. Pat. No. 3,911,534 to Henry J. Martens et al. which disclosures are incorporated herein by reference for a complete understanding of the locking device employed in the present invention. A discussion of the inventions in the field, known to the inventor, and their differences from the present invention is provided below.

U.S. Pat. Nos. 3,911,534 and 3,974,581 to Henry J. Martens et al. disclose a security tag having the pin contained on a first strip that is attached by a hinge to a second strip that has the locking component thereon. The hinged attachment may lead to the bending of the pin when contacting the locking component because of the predetermined arc that it must travel as a result of the hinged arrangement. Furthermore, the hinged arrangement allows the pin to protrude vertically when the device has fallen to the floor and may lead to injury. The '534 and '581 patents also disclose a pin soldered to a chain at one end and the other end of the chain riveted to the tag cover. The riveting of the chain on the outside of the tag body may subject the tag easy defeat by unscrupulous individuals. Furthermore, the pin thereof will protrude vertically when the device has fallen to the floor and may lead to injury.

U.S. Pat. No. 3,932,918 to Paskert discloses a releasably attachable clip for attachment to certain cloth articles, wherein the pin component is incorporated into the tag. However, the pin once again is held in a substantially hinged relation to the locking component and may lead to bending of the pin as a result of the arc which must be traveled in order to engage the locking component. Furthermore, the '918 patent may only be used with articles made of cloth and cannot engage solid components as disclosed in the instant invention.

U.S. Pat. No. 3,942,829 to Humble et al. discloses a security tag having the pin contained on a first strip that is attached by a hinge to a second strip that has the locking component thereon. The hinged attachment may lead to the bending of the pin when contacting the locking component because of the predetermined arc that it must travel as a result of the hinged arrangement. In addition, the hinged arrangement allows the pin to protrude vertically when the device has fallen to the floor and may lead to injury. Furthermore, the '829 patent may only be used with articles made of cloth and cannot engage solid components as disclosed in the instant invention.

U.S. Pat. No. 6,535,130 to Nguyen et al. discloses a complex electronic tag having visual and audible alarm systems incorporated into the tag body itself. The tag also incorporates a lanyard that is made of an electrical circuit wire that will cause an audible or visual alarm in the tag body to be activated should the lanyard be cut. The Nguyen device, however, uses a traditional independent pin having a head to attach the lanyard to an article, thereby possibly leading to work place injuries when the pin is dropped on the floor. Furthermore, the electrical components incorporated into each tag make the manufacture and use thereof cost prohibitive.

The prior art does not address the need for an integrated EAS tag that is difficult to defeat and easy to use. In addition, the prior art fails to provide a theft deterrent tag assembly that incorporates the pin, a lanyard and the tag body into one unit. Therefore, there remains a long standing and continuing need for an advance in the art of EAS and theft deterrent tags that makes the tags more difficult to defeat, simpler in both design and use, more economical and efficient in their construction and use, and provide a more secure engagement of the article.

SUMMARY OF THE INVENTION

Accordingly, it is a general object of the present invention to overcome the disadvantages of the prior art.

Therefore, it is a primary objective of the invention to provide an EAS tag wherein the tag body and the pin are an integrated unit.

It is another objective of the invention to provide a cost-efficient EAS tag.

It is another objective of the invention to provide an EAS tag that is durable.

It is a further objective of the invention to provide an EAS tag that is detachable when used with an authorized detaching unit.

It is a further objective of the invention to provide an EAS tag that provides an integrated pin to reduce the chances of injury to persons stepping on the pin, as is commonly a problem with the pins utilized in the prior art.

It is still a further objective of the invention to provide a theft deterrent device that can be quickly and easily secured to an article made of varying materials to prevent the unauthorized removal of the article.

It is yet a further object of the invention to provide a rugged theft deterrent unit to permit the repeated reuse thereof.

In keeping with the principles of the present invention, a unique EAS theft deterrent tag is disclosed wherein the pin element is integrated into the tag body via an elongated element. In integrating the pin component with the tag body, labor time and costs are reduced when removing the tag from an article being protected thereby because separate bins are not required for storing the tag body and the pin component until they are reused. In addition, labor time and costs during attachment of the tag body to an article are also reduced because the pin component is integrated therewith and a separate search for a corresponding pin is eliminated. In addition, the risk of work place injury is reduced because when the tag body falls on the floor, the pin also lays flat on the floor and should not penetrate the foot of an employee stepping thereon. Conversely, the pins illustrated in the prior art have a head on which the pin will rest and leave the shaft thereof in a vertical plane thereby increasing the risk of foot injuries.

Such stated objects and advantages of the invention are only examples and should not be construed as limiting the present invention. These and other objects, features, aspects, and advantages of the invention herein will become more apparent from the following detailed description of the embodiments of the invention when taken in conjunction with the accompanying drawings and the claims that follow.

BRIEF DESCRIPTION OF THE DRAWINGS

It is to be understood that the drawings are to be used for the purposes of illustration only and not as a definition of the limits of the invention. In the drawings, wherein similar reference characters denote similar elements throughout the several views:

FIG. 5 is a top perspective view of the tag of the instant invention showing an alternate preferred embodiment that does not incorporate electromagnetic components therein.

FIG. 7 is a perspective view of the tag of the instant invention showing an alternate preferred embodiment where the pin is not directly attached to the lanyard.

DETAILED DESCRIPTION OF THE INVENTION

Figure 1:
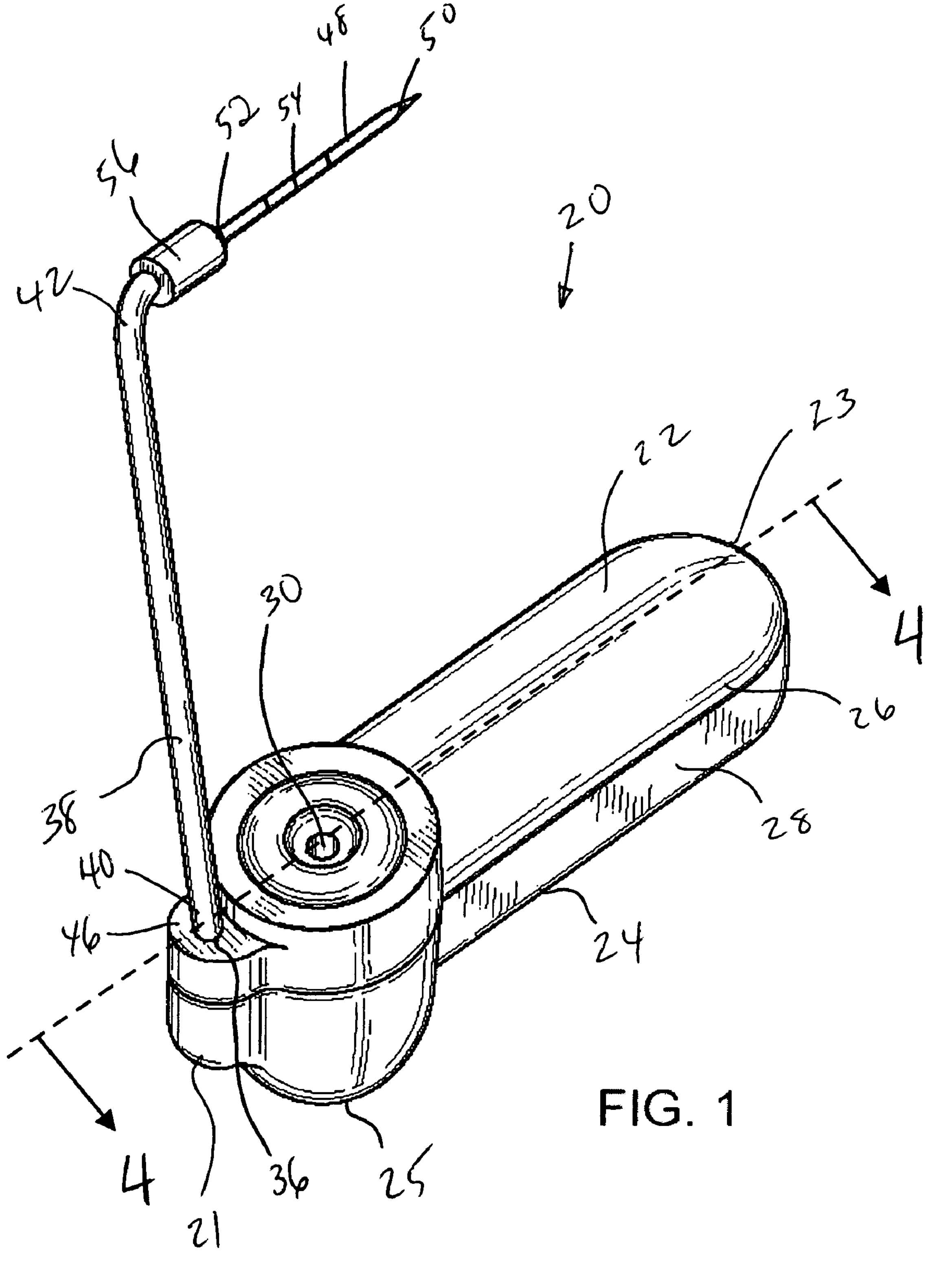
FIG. 1 is a top perspective view of the tag of the instant invention.
Figure 2:
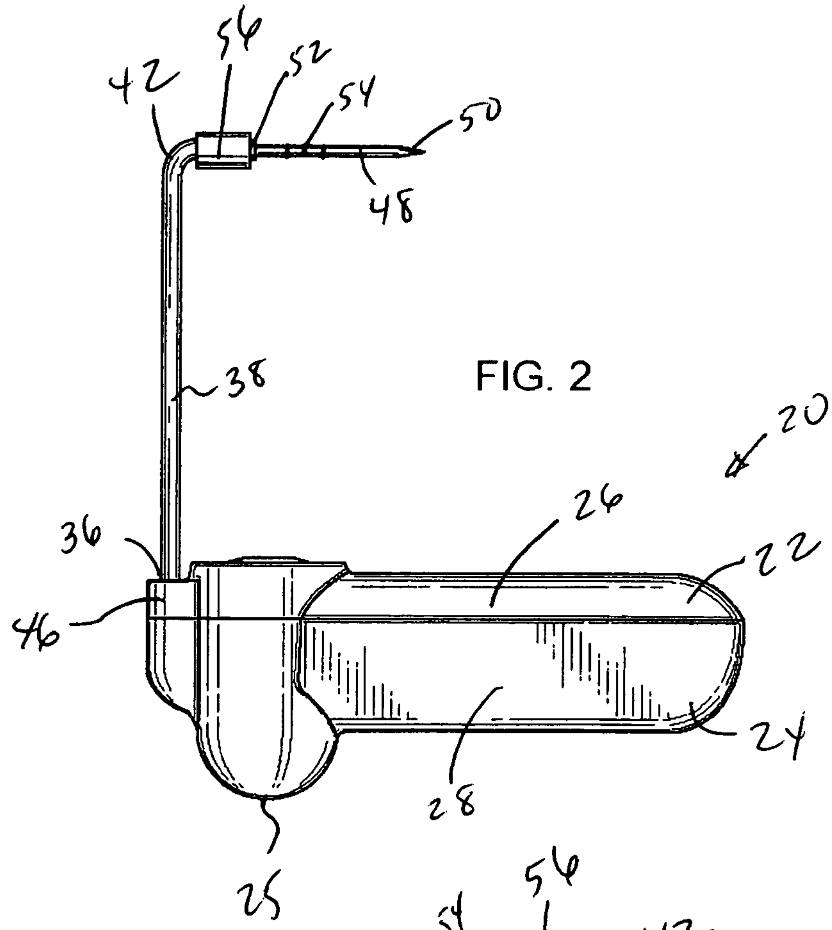
FIG. 2 is a side elevational view of the tag of the instant invention.
Figure 4:
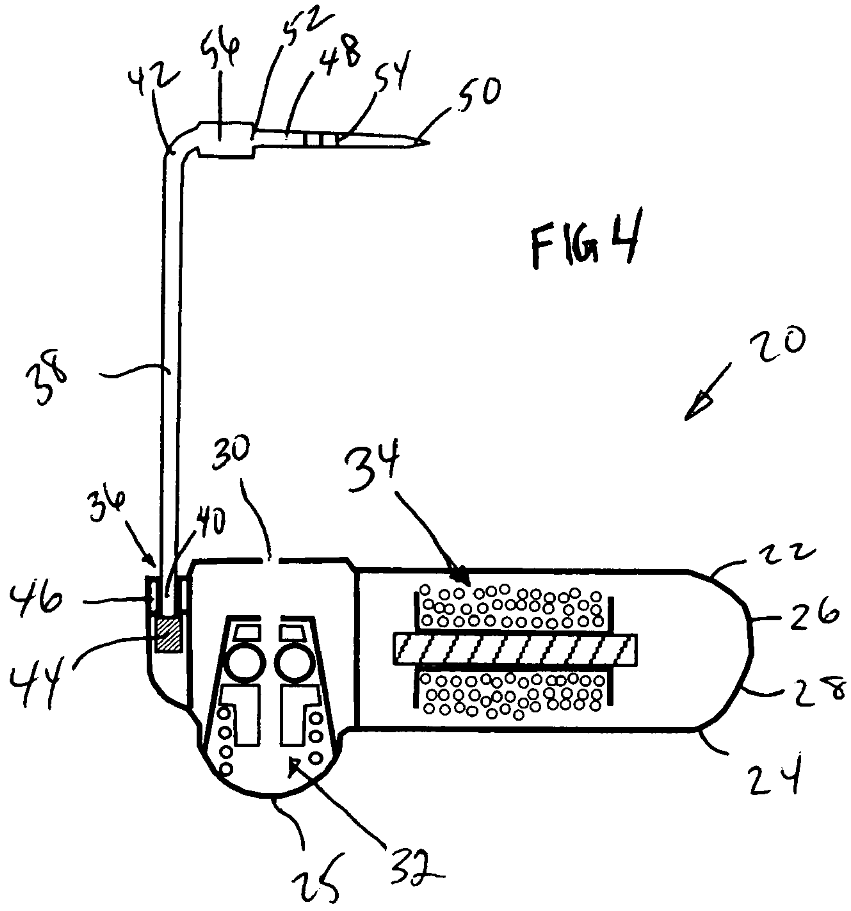
FIG. 4 is a cross sectional view of the tag of the instant invention taken along line 4-4 of FIG. 1.

Referring now to FIGS. 1, 2 and 4, a tag 20 is illustrated having a first half 22 and a second half 24. First and second halves 22 and 24 are preferably made of a hard or rigid material and are adapted to attach to one another and form a front end 21 and a rear end 23. A usable rigid or hard material might be a hard plastic such as, for purposes of illustration but not limitation, an injection molded ABS plastic. If a plastic material is used, the mating of a first side wall 26 to a second side wall 28 can be accomplished via an ultrasonic weld or like joining mechanism. However, it is to be understood that other joining methods, such as adhesives, may also be used. When first half 22 and second half 24 are securely joined, first sidewall 26 and second sidewall 28 form a peripheral outer wall of tag 20. Second half 24 has an apex region 25 that extends therefrom in an opposing direction to first half 22 in a substantially dome shaped manner. The dome shaped apex region 25 forces tag 20 to fall onto its side such that a pin 48 (described hereinafter) is not vertically oriented and prevents injury by accidentally stepping thereon.

An opening 30 is defined on first half 22 and is axially aligned with apex region 25. Apex region 25 encloses a locking mechanism 32. Locking mechanism 32 is not the subject of the instant invention and a detailed description thereof is disclosed in U.S. Pat. Nos. 3,858,280 and 3,911,534 to Martens et al., which is incorporated herein by reference. In addition, first half 22 and second half 24 enclose a resonant tag circuit 34 which is not the subject of the instant invention and a detailed description thereof is disclosed in my U.S. patent application Ser. No. 10/410,486, titled “Article Surveillance Tag Having a Metal Clip,” filed on Apr. 8, 2003, which is incorporated herein by reference. It is to be understood that alternate resonant tag circuitry that is known in the art may also be used with the instant invention. Resonant tag circuit 34 functions with electronic article surveillance systems that are well known in the art to prevent theft and similar unauthorized removal of articles from a controlled area.

An aperture 36 is defined through tag 20 to allow a lanyard 38, preferably formed of stainless steel cable, to pass therethrough. Lanyard 38 is flexible and has a first end 40 and a second end 42. First end 40 is inserted through aperture 36 and an anchor 44, having a greater diameter than aperture 36, is attached to first end 40. Anchor 44 may be formed by crimping a metal element onto first end 40 or by soldering thereon. In addition, anchor 44 may also preferably be formed by crimp splices. Anchor 44 securely maintains lanyard 38 within tag 20. A reinforcement wall 46, having a preferably tubular shape, extends inwardly from top half 22 and further defines aperture 36 such that a greater pull force would be required in order to pull lanyard 38 out of tag 20 through aperture 36. After lanyard 38 has passed through aperture 36 and anchor 44 engaged therein, first half 22 and second half 24 are sonic welded together, thereby enclosing anchor 44 therein.

Second end 42 of lanyard 38 receives a pin 48 thereon in substantially axial alignment. Pin 48 has a pointed end 50 and a dull end 52. Grooves 54 extend circumferentially along pin 48 and provide a more secure engagement when pin 48 is received within locking mechanism 32. Dull end 52 of pin 48 is attached to second end 42 of lanyard 38 by an attaching element 56. Attaching element 56 may be formed by crimping a metal element around dull end 52 and second end 42 or by soldering a metal element thereon, thereby permanently fixing the attaching element 56, dull end 52 and second end 42 together. In addition, attaching element 56 may also preferably be formed by crimp splices.

Figure 3:
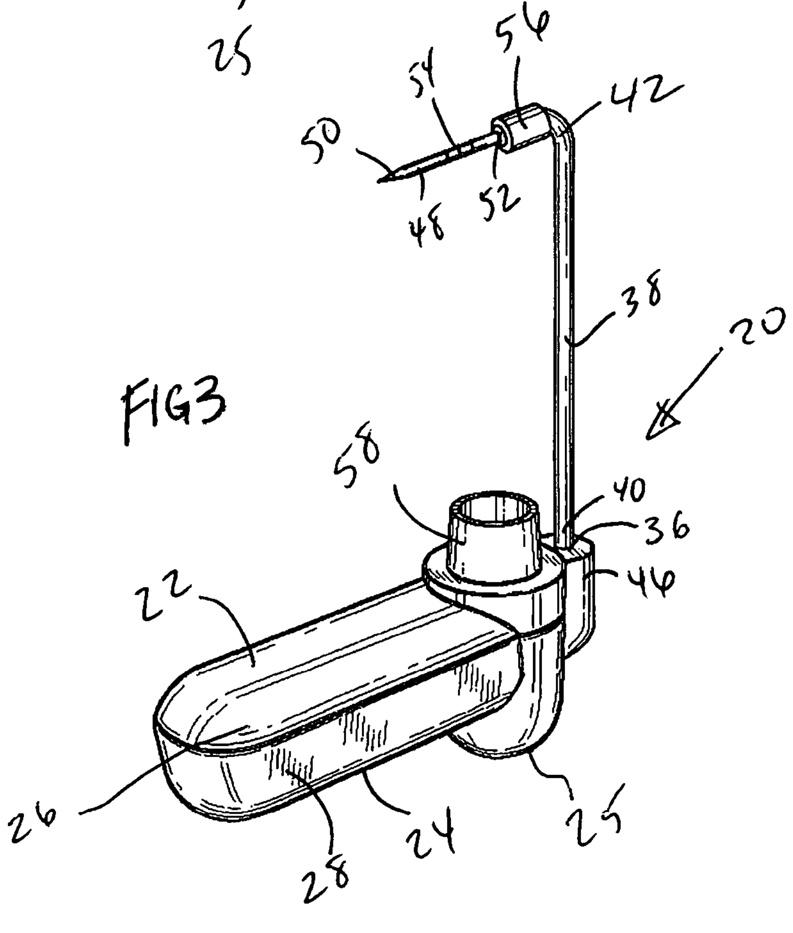
FIG. 3 is a perspective view of the tag of the instant invention showing an alternate preferred embodiment.

Now referring to FIG. 3, an alternate preferred embodiment of tag 20 is disclosed wherein an extension barrier 58 extends outwardly from first half 22 and substantially encircles opening 30. Extension barrier 58 is substantially tubular and is intended to prevent access to pin 48 when it is inserted within opening 30 and received within locking mechanism 32.

Figure 6:
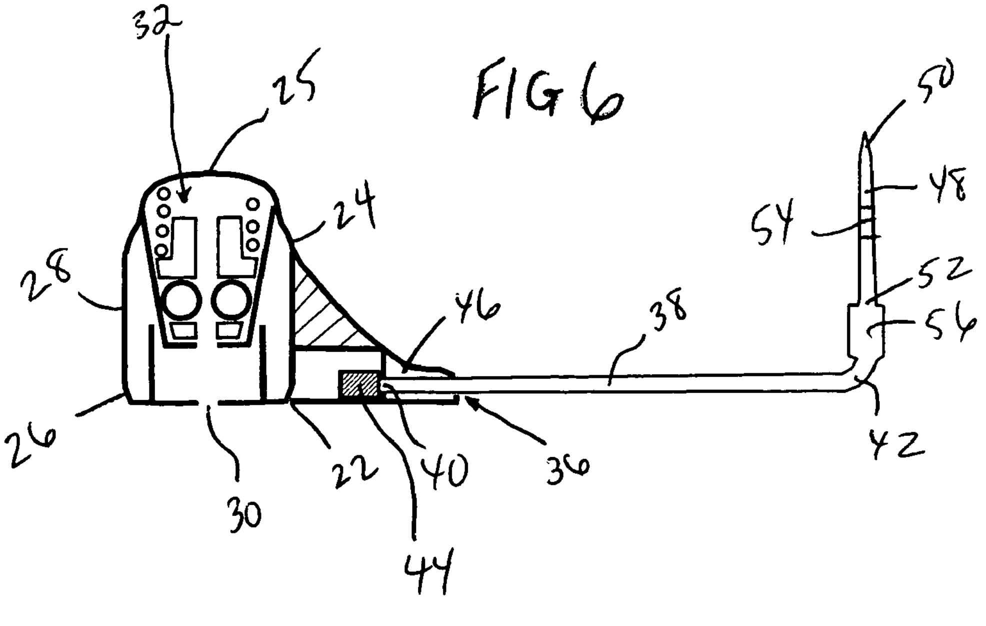
FIG. 6 is a cross sectional view of the tag of the instant invention taken along line 6-6 of FIG. 5.

Now referring to FIGS. 5, 6 and 7, an alternate preferred embodiment of tag 20 is disclosed wherein the resonant tag circuit 34 is removed in order to minimize the size of tag 20.

The alternate preferred embodiment is of compact size and is attachable to small articles, such as sunglasses, in order to provide theft deterrence.

Figure 8:
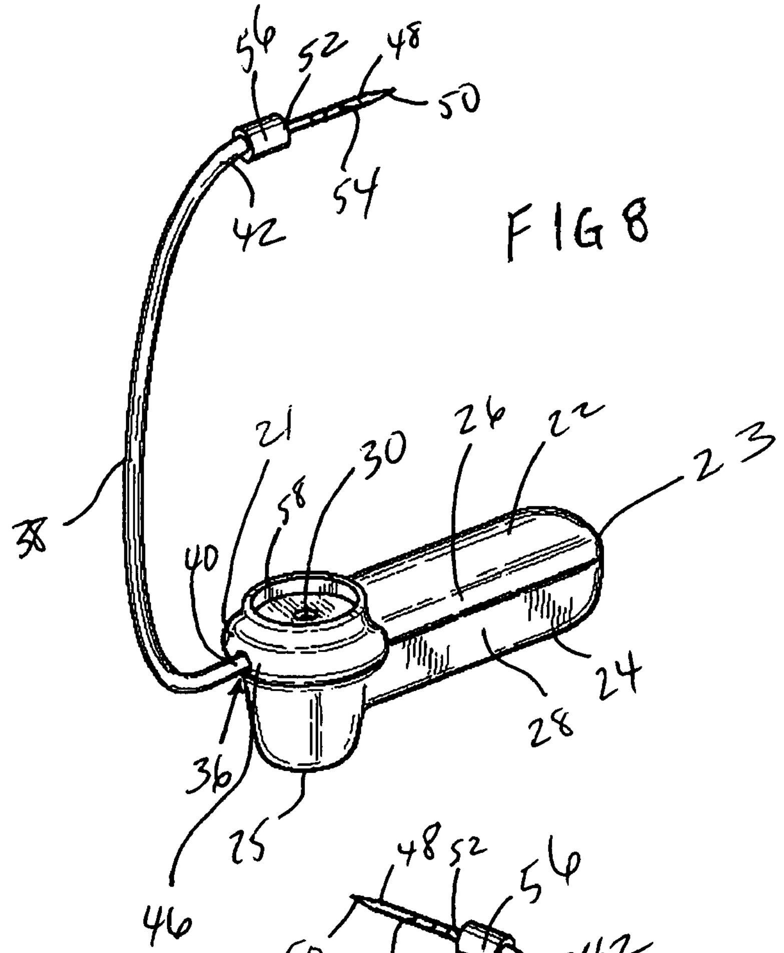
FIG. 8 is a perspective view of the tag of the present invention showing an alternate preferred embodiment thereof.
Figure 9:
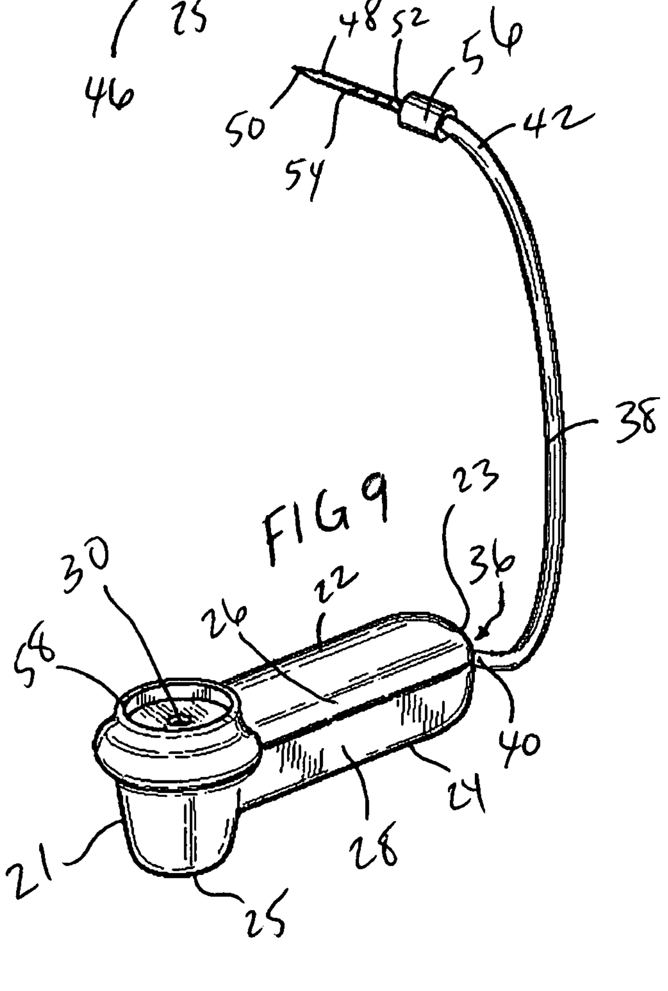
FIG. 9 is a perspective view of the tag of the present invention showing an alternate preferred embodiment thereof.

Now referring to FIG. 8, an alternate preferred embodiment of tag 20 is disclosed wherein the aperture 36 extends is defined by front end 21 and is perpendicular to the axis of opening 30. Now referring to FIG. 9, an alternate preferred embodiment of tag 20 is disclosed wherein the aperture 36 is defined by rear end 23 and is perpendicular to the axis of opening 30.

For attachment of tag 20 to articles of clothing, pointed end 50 of pin 48 passes through the article of clothing and is inserted into opening 30 and received within locking mechanism 32. For delicate fabrics, such as lingerie or silk blouses, the lanyard attaches around a portion of the article and forms a loop around the article when pin 48 is inserted into locking mechanism 32. Tag 20 may also be used with solid articles, such as baseball bats, wherein a loop is formed by the lanyard around the solid article (i.e. the handle of the baseball bat).

While the above description contains many specificities, these should not be construed as limitations on the scope of the invention, but rather as an exemplification of one preferred embodiment thereof. Many other variations are possible without departing from the essential spirit of the invention. Accordingly, the scope of the invention should be determined not by the embodiment illustrated, but by the appended claims and their legal equivalents.

What is claimed is:

1. An integrated theft deterrent device, comprising:

a tag body 20;

a locking mechanism 32 located within said tag body 20;

a lanyard 38 extending from within said tag body 20;

the lanyard 38 having a first end 40 and a second end 42, with the first end 40 inaccessibly coupled within an aperture 36 of the tag body 20 by an anchor 44 attached to the first end 40;

a pin 48 being permanently connected to the second end of said lanyard 38 at an end opposing said tag body 20;

an apex region 25 extending from said tag body 20 such that the apex region 25 causes the tag body 20 to a side such that the pin 48 is maintained in horizontal alignment with a flat surface to prevent injury from stepping thereon;

a first half 22 and a second half 24 that are joined around a perimeter of said tag body 20 by a first side wall 26 and a second side wall 28 extending inwardly from said first and second halves respectively;

the opening 30 being defined by said first half 22 for receiving said pin 48; and the aperture 36 being defined by said first half 22 through which said lanyard 38 emanates;

with said pin 48 received within said locking mechanism 32 in a secure yet detachable manner; and wherein said integrated theft deterrent device does not include a power source.

2. The device of claim 1, wherein said apex region 25 is substantially dome shaped.

3. The device of claim 1, wherein said tag body 20 defines the aperture 36, said aperture 36 being sufficiently sized to allow said lanyard 38 to pass therethrough yet preventing said anchor 44 from being withdrawn.

4. The device of claim 1, wherein a reinforcement wall 46 extends inwardly into said tag body 20 and farther defines said aperture 36.

5. The device of claim 1, wherein said first end 40 is attached to said anchor 44 by crimping.

6. The device of claim 1, wherein said first end 40 is attached to said anchor 44 by soldering.

7. The device of claim 1, wherein said lanyard 38 is made of stainless steel cable yet is flexible.

8. The device of claim 1, wherein said tag body 20 further comprises a resonant tag circuit.

9. The device of claim 8, wherein said aperture 36 is sufficiently sized to allow said lanyard 38 to pass therethrough yet preventing said anchor 44 from being withdrawn.

10. The device of claim 8, wherein a reinforcement wall 46 extends inwardly from said first half into said tag body 20 and further defines said aperture 36.

11. The device of claim 8, wherein said first end 40 is attached to said anchor 44 by crimping.

12. The device of claim 8, wherein said first end 40 is attached to said anchor 44 by soldering.

13. The device of claim 8, wherein said lanyard 38 is made of flexible stainless steel cable.

14. A method of manufacturing an integrated theft deterrent device, comprising the steps of:

providing a tag body 20;

providing a first half 22 and a second half 24 that are joined around a perimeter of said tag body 20 by a first side wall 26 and a second side wall 28 extending inwardly from said first and second halves respectively;

defining an aperture 36 being through said first half 22 through which said lanyard 38 emanates; whereby a first end 40 of the lanyard 38 is maintained by the tag body 20;

defining an opening 30 through said first half 22 for receiving said pin 48 attached to a second end of lanyard 38;

providing a locking mechanism 32 within said tag body 20;

excluding a battery from within said tag body;

providing an apex region 25 on tag body 20 such that said pin 48 is maintained in horizontal alignment with a flat surface on which the tag body 20 rests to prevent injury from stepping on said pin 48.

15. An integrated theft deterrent device, comprising:

a tag body 20;

a locking mechanism 32 located within said tag body 20;

a lanyard 38 extending from within said tag body 20;

a pin 48 being permanently connected to the second end of said lanyard 38 at an end opposing said tag body 20, with said pin 48 received within said locking mechanism 32 in a secure yet detachable manner;

a first half 22 and a second half 24 that are joined around a perimeter of said tag body 20 by a first side wall 26 and a second side wall 28 extending inwardly from said first and second halves respectively;

the opening 30 being defined by said first half 22 for receiving said pin 48; and the aperture 36 being defined by said first half 22 through which said lanyard 38 emanates;

an apex region 25 extending from said tag body 20 such that the apex region 25 causes the tag body 20 to a side such that the pin 48 is maintained in horizontal alignment with a surface to prevent injury from stepping thereon; and wherein said integrated theft deterrent device does not include a power source and the lanyard does not form and complete an electrical circuit.

16. The integrated theft deterrent device of claim 15, wherein:

the lanyard 38 has a first end 40 and a second end 42, with the first end 40 permanently and irremovably coupled within an aperture 36 of the tag body 20 by an anchor 44 attached to the first end 40.

17. The method of claim 14, further comprising the step of enclosing a resonant tag circuit 34 within said tag body.

18. The integrated theft deterrent device of claim 15, wherein a resonant tag component 34 is located within said tag body 20.

* * * * *